(12) United States Patent
Sonkusale et al.

(10) Patent No.: US 11,547,358 B2
(45) Date of Patent: Jan. 10, 2023

(54) THREAD-BASED OXYGEN SENSOR

(71) Applicants: Trustees of Tufts College, Medford, MA (US); DTAMedical, Loulle (FR)

(72) Inventors: Sameer Sonkusale, Lincoln, MA (US); Junfei Xia, Allston, MA (US); Francois Dufay, Loulle (FR)

(73) Assignees: Trustees of Tufts College, Medford, MA (US); DTAMedical, Loulle (FR)

( * ) Notice: Subject to any disclaimer, the term of this patent is extended or adjusted under 35 U.S.C. 154(b) by 0 days.

(21) Appl. No.: 17/545,151

(22) Filed: Dec. 8, 2021

(65) Prior Publication Data
US 2022/0283113 A1 Sep. 8, 2022

Related U.S. Application Data

(60) Provisional application No. 63/156,640, filed on Mar. 4, 2021.

(51) Int. Cl.
*A61B 5/00* (2006.01)
*A61B 5/145* (2006.01)
*A61B 5/1473* (2006.01)

(52) U.S. Cl.
CPC .......... *A61B 5/6837* (2013.01); *A61B 5/1473* (2013.01); *A61B 5/14546* (2013.01); *A61B 5/445* (2013.01); *A61B 5/14507* (2013.01); *A61B 5/14542* (2013.01)

(58) Field of Classification Search
CPC ............ A61B 5/14542; A61B 5/14546; A61B 5/1468–1473; A61B 5/1477; A61B 2562/02; A61B 5/145; A61B 5/14503; A61B 5/14507; A61B 5/1451; A61B 5/14517; A61B 5/14532; A61B 5/14539; A61B 5/445; A61B 5/6801; A61B 5/6804; A61B 5/6837; A61B 5/6883;
(Continued)

(56) References Cited

U.S. PATENT DOCUMENTS 5,985,129 A 11/1999 Gough et al.
7,544,886 B2 6/2009 Detian et al.
(Continued)

FOREIGN PATENT DOCUMENTS

| WO | WO-2017189966 A1 * | 11/2017 | ........... A61B 5/6804 |
| WO | WO-2020106353 A1 * | 5/2020 | ......... A61B 5/14517 |
| WO | WO-2020201741 A1 * | 10/2020 | ......... A61B 5/14503 |

OTHER PUBLICATIONS

P. Mostafalu, W. Lenk, M. R. Dokmeci, B. Ziaie, A. Khademhosseini and S. R. Sonkusale, "Wireless Flexible Smart Bandage for Continuous Monitoring of Wound Oxygenation," in IEEE Transactions on Biomedical Circuits and Systems, vol. 9, No. 5, pp. 670-677, Oct. 2015, doi: 10.1109/TBCAS.2015.2488582. (Year: 2015).*
(Continued)

*Primary Examiner* — Eric F Winakur
*Assistant Examiner* — Alice Ling Zou
(74) *Attorney, Agent, or Firm* — Occhiuti & Rohlicek LLP

(57) ABSTRACT

An oxygen sensor for sensing dissolved oxygen concentration in tissue includes an electrochemical sensor comprising first and second conductive threads having proximal sections connected to a potentiostat. The first thread forms a cathode, and the second thread forms an anode.

18 Claims, 4 Drawing Sheets

(58) Field of Classification Search
CPC ... A61B 2562/12–125; A61F 13/00051; A61F 2013/0094; A61F 2013/0097
See application file for complete search history.

(56) References Cited

U.S. PATENT DOCUMENTS

| | | | |
|---|---|---|---|
| 2007/0027385 A1* | 2/2007 | Brister | A61B 5/6848 600/347 |
| 2007/0106143 A1* | 5/2007 | Flaherty | A61N 1/0531 607/116 |
| 2009/0048635 A1* | 2/2009 | Andino | A61N 1/0468 607/2 |
| 2011/0108439 A1 | 5/2011 | Gourishankar et al. | |
| 2016/0153927 A1 | 6/2016 | Kirsch et al. | |
| 2018/0228436 A1* | 8/2018 | Sonkusale | G01N 27/403 |

OTHER PUBLICATIONS

M. Punjiya, H. R. Nejad, P. Mostafalu and S. Sonkusale, "pH sensing threads with CMOS readout for Smart Bandages," 2017 IEEE International Symposium on Circuits and Systems (ISCAS), 2017, pp. 1-4, doi: 10.1109/ISCAS.2017.8050730. (Year: 2017).*
Kudo, H., Iguchi, S., Yamada, T. et al. A flexible transcutaneous oxygen sensor using polymer membranes. Biomed Microdevices 9, 1 (2007). https://doi.org/10.1007/s10544-006-9000-z (Year: 2007).*
Wei et al. "Review of Dissolved Oxygen Detection Technology: From Laboratory Analysis to Online Intelligent Detection" Sensors Sep. 16, 2019 (Sep. 16, 2019), entire document.

* cited by examiner

THREAD-BASED OXYGEN SENSOR

CROSS-REFERENCE TO RELATED APPLICATIONS

This application claims priority to U.S. Application Ser. No. 63/156,640, filed on Mar. 4, 2021, the content of which is incorporated herein by reference.

BACKGROUND

Oxygen plays a key role in human physiology. For example, it is used in energy production through cellular respiration. It also participates in various bodily function ranging from memory storage and cognitive function to tissue repair and regeneration during would healing. A lack of oxygen in tissue or blood is associated with many diseases, such as cerebral ischemia, congestive heart failure, and cancer.

In addition, oxygen is abnormally modulated in various diseases. As a result, in situ monitoring of oxygen is an important biomarker for assessing insufficient oxygen delivery and the resulting tissue damage.

A lack of oxygen is of particular importance in the context of wound healing. The process of healing a would is characterized by the stepwise inflammation, proliferation, and remodeling phases. Disruption of these phases, for example by lack of oxygen, can lead to a chronic wound. The level of tissue oxygenation is thus an important biomarker in the process of wound healing.

Known oxygen sensors only measure superficial oxygen levels in a shallow wound bed. However, these oxygen levels, even if accurately determined, will differ from that present deep in the tissue. This is because oxygen at or near the surface equilibrates with atmosphere oxygen levels.

A difficulty that arises in known oxygen sensors is that it is difficult to measure oxygen levels deep inside tissue. This can occur as a result of a mismatch between the electrode and the tissue at the interface between the two structures.

Known oxygen sensors include those that rely on interaction between dissolved oxygen and electromagnetic waves, particularly in the near infrared. However, electromagnetic waves tend to attenuate when passing through bodily fluids. As a result, it is difficult to use them to measure dissolved oxygen concentrations deep in the body.

SUMMARY

In one aspect, the invention features an apparatus for sensing dissolved oxygen concentration in tissue. Such an apparatus includes an oxygen sensor having an electrochemical sensor that comprises first and second conductive threads having proximal sections connected to a potentiostat. The first thread forms a cathode; the second thread forms an anode.

Embodiments include those in which one or more of the threads includes silver, those in which one or more of the threads include gold, and those in which one or more of the threads include platinum.

In some embodiments, the second thread includes a bare distal section, and a shielded section between the proximal and distal sections. Among these are embodiments in which the electrochemical sensor is a wire-type sensor having an extended sensing zone and the first thread includes a bare distal section and a shielded section between the proximal and distal sections. Also among these embodiments are those in which electrochemical sensor is a tip-type sensor and the first thread includes a shielded distal section having an exposed distal tip that defines a distal sensing zone.

Some embodiments include hydrogel in contact with one or more of the threads.

In some embodiments, one or more of the threads comprises a wire.

Embodiments further include those in which the electrochemical sensor comprises a distal tip that defines a distal sensing zone, hydrogel at the distal tip, and an oxygen-permeable membrane disposed over the hydrogel.

Other embodiments include a pad. In such embodiments, the electrochemical sensor is a wire-type sensor having an extended sensing zone that is disposed on the pad.

In still other embodiments, the electrochemical sensor is a wire-type sensor having an extended sensing zone that is covered with hydrogel.

DETAILED DESCRIPTION

As a result of its ability to conform to the human body, its mechanical stability, and its low cost, a suitably modified thread is useful has a point-of-care biosensor. Advantages of thread-based sensors include the ability to manufacture than without a cleanroom, the large surface area available to interface with an analyte, and its ability to wick.

Unlike rigid metal electrodes, a thread-based electrode is easily inserted inside tissue using only a suture needle. This permits measurements deep in the tissue.

Figure 1:
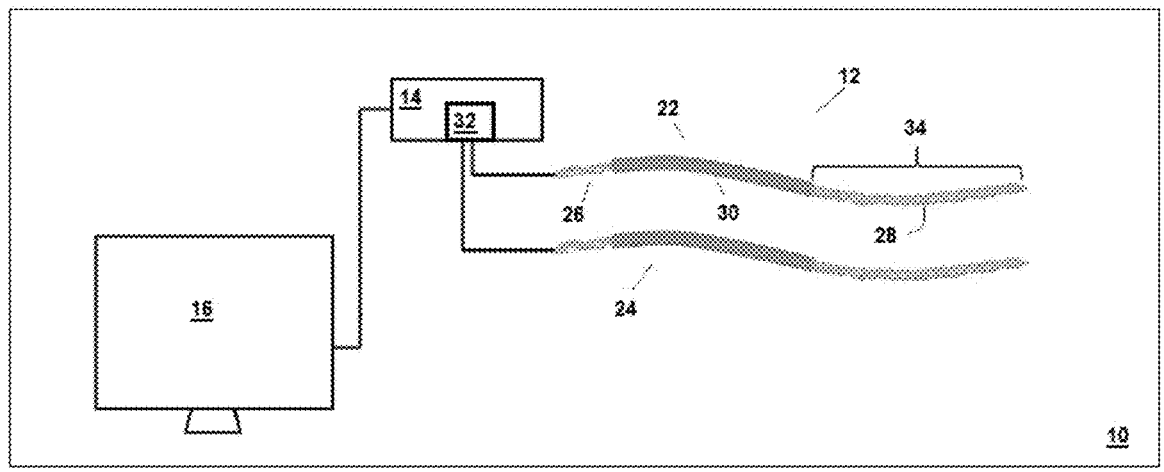
FIG. 1 shows a wire-type oxygen sensor.
Figure 2:
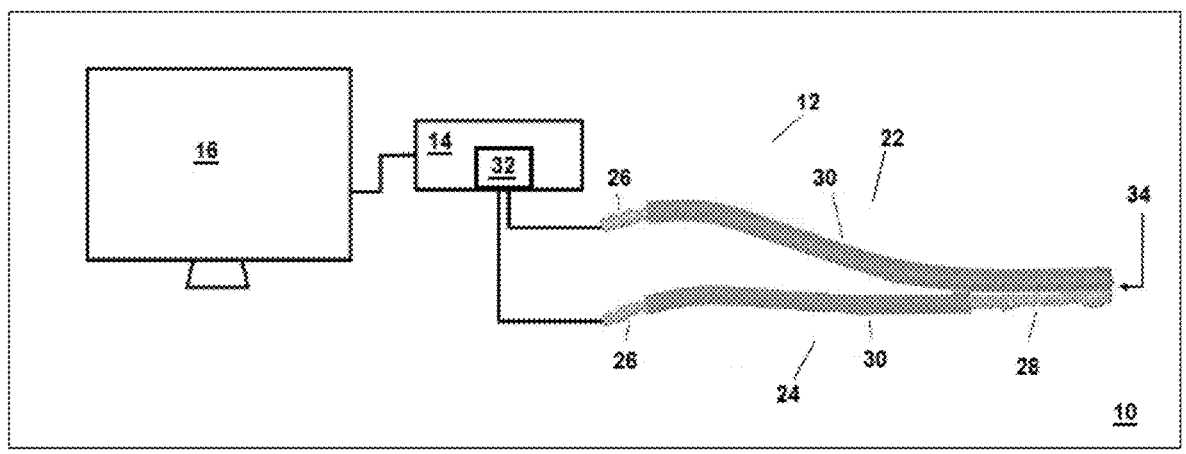
FIG. 2 shows a tip-type oxygen sensor.

FIGS. 1 and 2 shows two embodiments of an oxygen sensor 10 that relies on threads that have been processed to form thread-based electrochemical sensors. Such sensors are useful for monitoring concentration of dissolved gas, and in particular, dissolved oxygen. The oxygen sensor 10 includes an electrochemical sensor 12 that is connected to read-out electronics 14 connected to a display 16.

FIGS. 1 and 2 show different types of electrochemical sensor 12.

Figure 3:
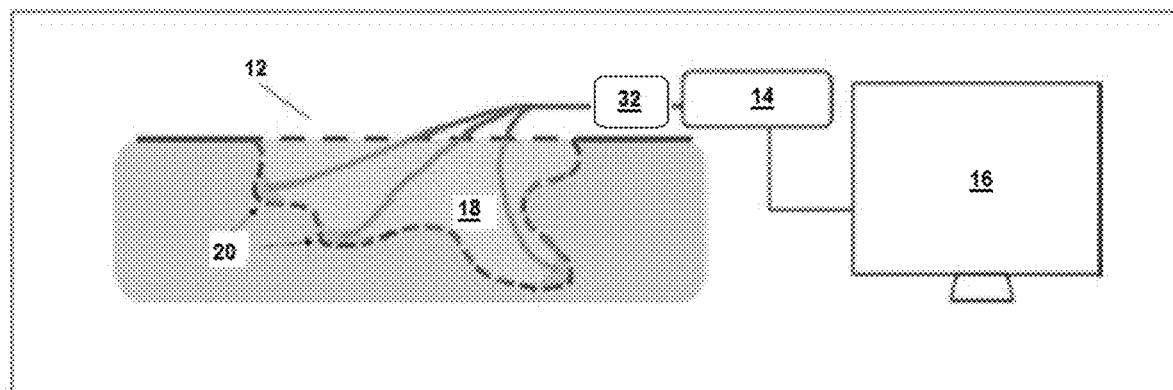
FIG. 3 shows multiple tip-type sensors deployed in a wound bed.

The electrochemical sensor 12 shown in FIG. 1 is a wire-type sensor that is useful for measuring an average oxygenation level across an extended region, such as across a wound bed 18, such as that shown in FIG. 3. That shown in FIG. 2 is a tip-type sensor that is particularly useful for pinpointing a region-of-interest 20 within the wound bed 18.

Referring to FIG. 1, the wire-type sensor 12 comprises first and second threads 22, 24, each of which incorporates a conductive material. A suitable choice of conductive material is a conducting metal that is also biocompatible. Suitable metals include silver, gold, and platinum.

Each thread 22, 24 comprises a bare proximal section 26 and a bare distal section 28 separated by a shielded section 30 that is shielded by a dielectric jacket. Each thread connects to a potentiostat 32 at its proximal section 26. As a result, the first thread 22 serves as a cathode and the second thread 24 serves as an anode. The combination thus forms an electrochemical sensor having a sensing zone 34 that extends along the distal sections 28 of the threads.

In the alternative embodiment shown in FIG. 2, an electrochemical sensor 12 implemented as a tip-type sensor comprises first and second threads 22, 24, each of which incorporates a conductive material. A suitable choice of conductive material is a conducting metal that is also biocompatible. Suitable metals include silver, gold, and platinum.

The first thread 22 comprises a bare proximal section 26. The shielded section 30 covers all but the distal tip of the distal section 28, thus leaving only the distal tip as a sensing zone 34. The second thread 24 has a bare proximal section 26 and a distal section 28 separated by a shielded section 30 that is shorter than that of the first thread 24, thus leaving a larger exposed section.

The proximal sections 26 of the first and second threads 22, 24 connect to corresponding terminals of the potentiostat 32. As a result, the first thread 22 serves as a cathode and the second thread 24 serves as an anode. The combination thus forms an electrochemical sensor having a sensing zone 30 confined to the distal tip of the first thread 22.

In the foregoing embodiments, the cathode is a noble metal that is stable and that does not participate in electrode reactions. Examples of suitable materials include silver and gold. In some embodiments, the anode is a silver-coated thread, and the cathode is a gold wire.

In some embodiments, during operation, the exposed surfaces are covered by a material that suppresses the tendency for fouling during extended use. Suitable materials include a hydrogel.

In operation, the potentiostat 32 provides a steady voltage that drives a current. The current's magnitude is indicative of dissolved oxygen concentration.

In general, there are two major types of electrochemical oxygen sensors: galvanic and polarographic. In a galvanic sensor, two dissimilar metals are paired as anode and cathode. When connected, an output voltage or current is spontaneously generated in response to change in oxygen level. In a polarographic sensor, an external voltage source is applied to both electrodes and the output current is measured. The use of threads as described herein is applicable to both types.

Figure 4:
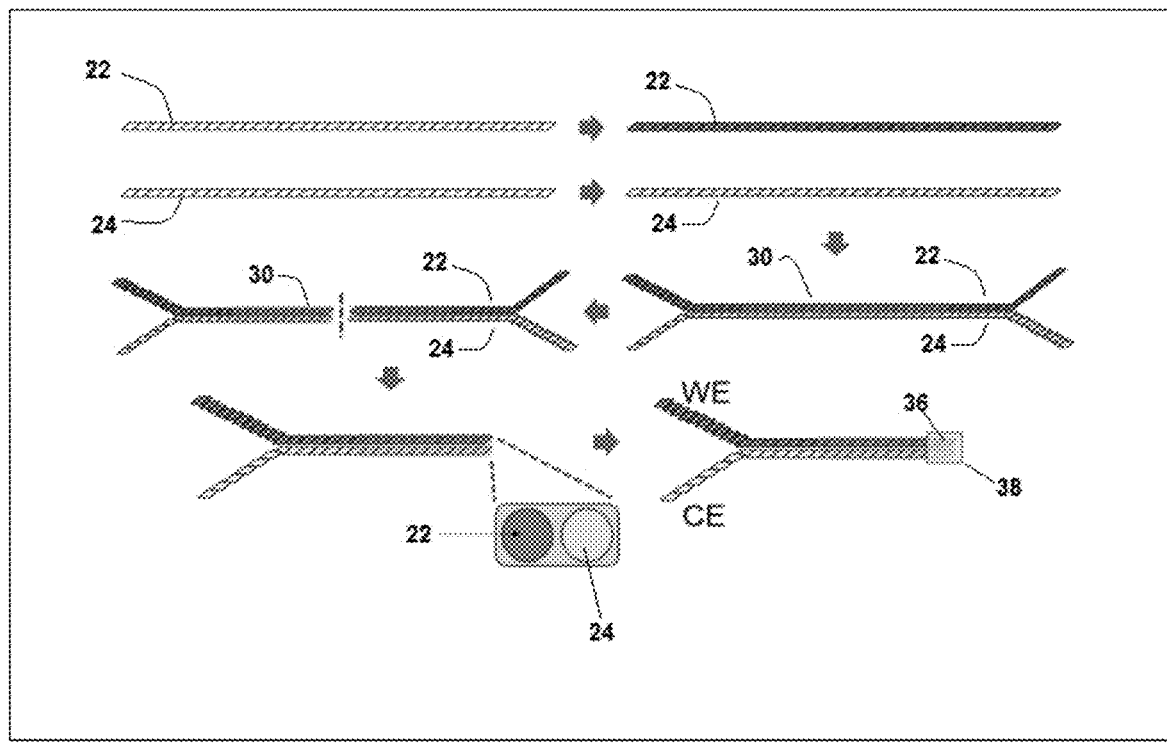
FIG. 4 shows steps in the manufacture of an electrochemical sensor.

Referring to FIG. 4, a suitable method of making an oxygen sensor 10 includes coating a first thread 22 with carbon ink, coating a second thread 24 with silver or gold ink, and bundling them together with a dielectric ink to form a shielded section 30. In some embodiments, the first and second threads 22, 24 comprise polyester. The threads are then sliced to expose cross-sections thereof.

Zinc is then electrochemically deposited on a cross-section of the first thread 22. This becomes a working electrode WE. The second thread's end becomes the counter electrode CE.

The tips of the threads 22, 24 are then coated with an electrolyte gel 36 and sealed with a protective oxygen-permeable membrane 38. In the illustrated embodiment, the membrane 38 is PDMS. A suitable electrolyte gel 36 is 0.1 mM KOH in agarose.

Although it is permeable to oxygen, the membrane 38 hinders oxygen diffusion to some extent, thus lowering temporal resolution. The temporal resolution can thus be controlled by controlling the membrane's thickness.

To carry out electrochemical measurements, the sensor 12 is connected to a potentiostat 32, which carries out chrono-amperometry at a polarographic voltage of 0.7 volts.

An impediment to the use of a thread 22, 24 as an electrode arises from the inherently non-planar surface at the thread's tip and from the thread's natural wicking properties. The coating of electrolyte gel 36 and the sealing with PDMS 38 co-operate to ameliorate these difficulties. Moreover, because the electrode area is small, the overall output current is small, thus slowing consumption of zinc. In addition, being a polarographic sensor, no current is generated when the sensor 12 is turned off. These properties promote a long-lived sensor 12 that can be used for extended periods to monitor oxygen in a chronic wound.

In some embodiments, rather than carrying out electrochemical deposition of zinc, it is useful to provide a commercially-available silver-coated thread. As silver is not an active metal, it is necessary to apply an external voltage to trigger the electrode reaction, in which silver is dissolved at the anode and oxygen reacts with water at the cathode. In preferred embodiments, the cathode is a noble metal that is stable and that does not participate in electrode reactions. In the following two types of sensor, gold and silver are selected as cathode materials, respectively.

Some embodiments of a flexible, thread-based electrochemical sensor along the lines of the foregoing respond to change in dissolved oxygen concentrations and does so linearly within a range of 2.94-47.86 milligrams per liter of dissolved oxygen with a sensitivity of 624.17 nanoamperes per milligram-liter of dissolved oxygen. The sensor shows good repeatability with data variation less than 2%. The sensor also displays relatively good stability over the period of one week in a simulated tissue environment. Such a sensor can be easily placed and secured in the wound bed using non-toxic PDMS as a supporting material.

Figure 5:
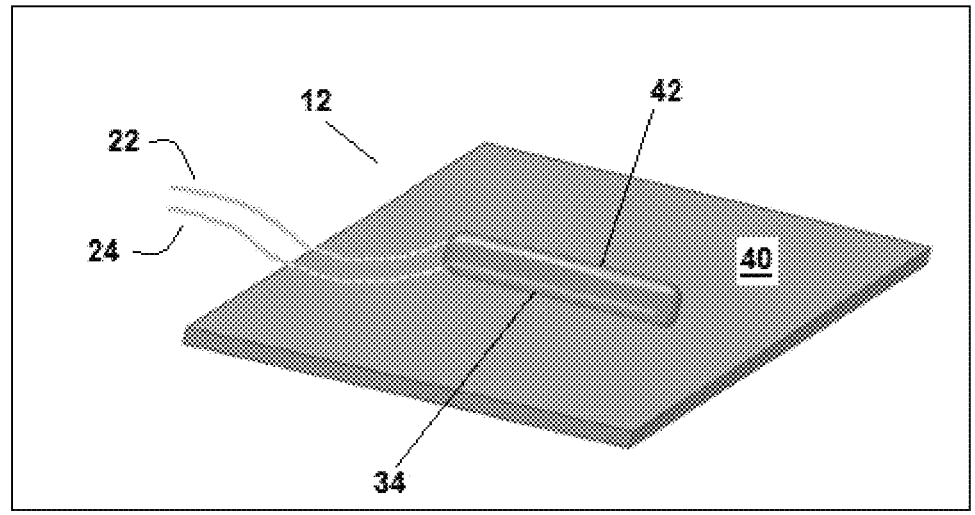
FIG. 5 shows a hydrogel-coated wire sensor on a pad.

In some embodiments, the sensor 12 comprises silver-coated first and second threads 22, 24 that have been cleaned by isopropanol and cut into ten-centimeter segments, of which two centimeters is used as a sensing zone 34 and fixed onto a thin PDMS pad 40, as shown in FIG. 5. The remaining segments are pulled to the other side of the pad using a needle. The connection point is then sealed with dielectric ink. The sensing zone 34 is then coated with a gel layer 42. The gel layer 42 ensures the presence of electrolytes for the electrode reactions. A suitable material for the gel layer 42 is hydrogel.

The sensor 12 can be easily applied to a wound bed 18 with the gel layer 42 facing inward. Such design allows easy connection to a readout electronics 14. The transparency of the PDMS pad 40 and gel layer 42 makes it possible to continue to visually monitor the wound bed 18. The length of the sensing zone 34 can be freely adjusted depending on the area of the wound bed 18.

The shape of the sensing zone 34 can be adjusted as well due to the flexible nature of the thread. For example, FIG. 6 shows an L-shaped sensing zone 34 and FIG. 7 shows a Z-shaped sensing zone 34.

Figure 6:
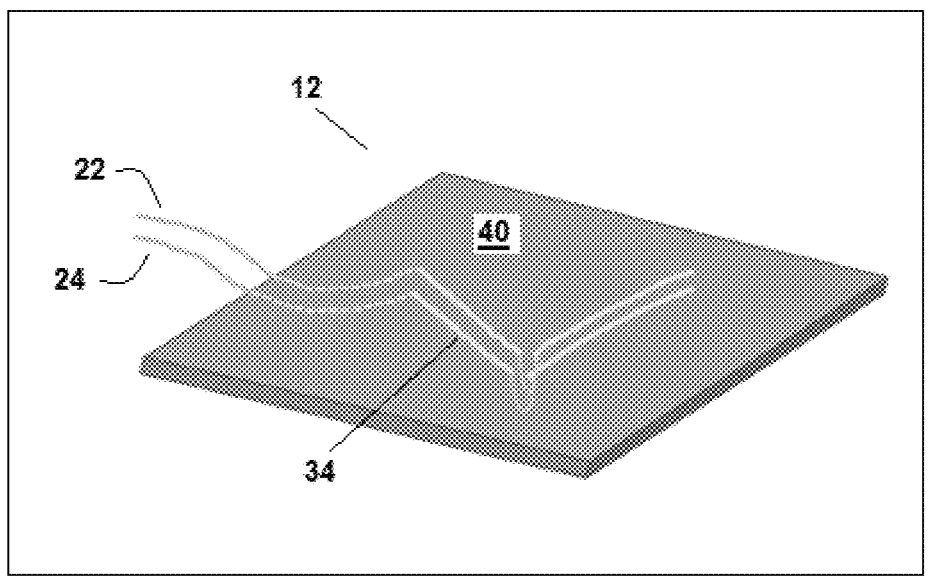
FIGS. 6 and 7 show wire sensors bent into shapes to conform to wound geometry.
Figure 7:
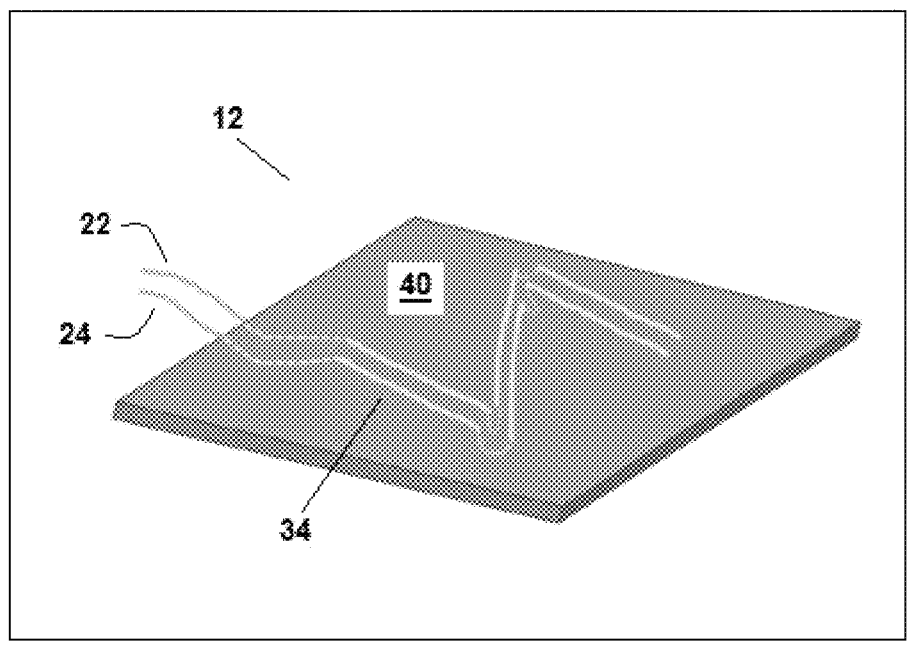

As is apparent from FIGS. 6 and 7, the first and second threads 22, 24 can be placed into the wound bed 18 without the gel layer 42 provided that the tissue itself provides sufficient concentration of ions, particularly chloride ions, for the reaction.

However, a gel layer 42 has additional advantages. These include protecting the sensing zone 34 from mechanical abrasion, such as that caused by displacement. In addition, the gel layer 42 provides protection from toxicity, if any, induced by the thread 22, 24 or the electrode reactions. Although a gel layer 42 inevitably hinders oxygen diffusion, it does not do so to an appreciable extent.

In some embodiments, it is useful to take measures to avoid having the measured oxygen concentration be affected by oxygen in the atmosphere that may diffuse through the PDMS pad 40. Such measures include embedding the sensor 12 inside the tissue or coating the PDMS pad 40 with an oxygen-diffusion barrier, examples of which include PPC and PVA membrane.

The principles described herein can also be used to sense other analytes, such as glucose, or to sense pH or pOH. A glucose sensor is implemented by implemented by immobilizing glucose oxidase enzyme at the sensing zone 34 using a matrix, such as chitosan or another polymer. A pH sensor is implemented by coating the sensing zone 34 with polyaniline. on the conductive tip.

Other embodiments feature those in which the sensing zone 34 has been functionalized to detect other ions, such as sodium ions and potassium ions, or other analytes, such as lactate. In still other embodiments, the sensing zone 34 is functionalized with antibodies or aptamers for detection of target biomolecules, including nucleic acids, such as DNA and RNA, and proteins and amino acids.

The invention claimed is:

1. An apparatus comprising an oxygen sensor for sensing dissolved oxygen concentration in tissue in a wound bed, said oxygen sensor comprising an electrochemical sensor configured for measuring an oxygenation level in said wound bed, said electrochemical sensor comprising a cathode and an anode, wherein said cathode comprises a first conductive thread, wherein said anode comprises a second conductive thread, wherein said first and second conductive threads have proximal sections connected to a potentiostat, wherein said second conductive thread has a bare distal section and a shielded section that extends between said proximal section and said bare distal section, wherein one or more of said threads comprises gold, and wherein said electrochemical sensor has an adjustable sensing zone.

2. The apparatus of claim 1, wherein one or more of said threads comprises silver.

3. The apparatus of claim 1, wherein one or more of said threads comprises platinum.

4. The apparatus of claim 1, wherein said first thread is coated with carbon ink, wherein said second thread is coated with gold ink, and wherein said shielded section comprises dielectric ink that bundles together said first and second threads.

5. The apparatus of claim 4, wherein said electrochemical sensor is a tip-type sensor that is configured to measure an oxygenation level at a region-of-interest within said wound bed, wherein said first thread comprises a shielded distal section having an exposed distal tip that defines a distal sensing zone and wherein said shielded distal section of said first thread faces said bare distal section of said second thread.

6. The apparatus of claim 1, wherein said electrochemical sensor is a wire-type sensor having an extended sensing zone to permit measurement of an average oxygenation level across said wound bed, wherein said first thread comprises a bare distal section, a bare proximal section, and a shielded section that extends from said bare proximal section to said bare distal section, and wherein said bare distal section of said second thread faces said bare distal section of said first thread.

7. The apparatus of claim 1, further comprising hydrogel in contact with one or more of said threads.

8. The apparatus of claim 1, wherein one or more of said threads wicks.

9. The apparatus of claim 1, wherein said cathode comprises said thread having gold incorporated therein and said anode comprises a silver-coated thread.

10. The apparatus of claim 1, wherein said cathode comprises gold and wherein said anode comprises silver.

11. The apparatus of claim 1, wherein said electrochemical sensor comprises a galvanic sensor.

12. The apparatus of claim 1, wherein said electrochemical sensor comprises a polarographic sensor.

13. The apparatus of claim 1, wherein said electrochemical sensor comprises a distal tip of said distal section that defines a distal sensing zone, hydrogel at said distal tip and an oxygen-permeable membrane disposed over said hydrogel to seal said distal tip.

14. The apparatus of claim 1, further comprising a pad, wherein said electrochemical sensor is a wire-type sensor having an extended sensing zone that is disposed on said pad.

15. The apparatus of claim 1, wherein said electrochemical sensor is a wire-type sensor having an extended sensing zone that is covered with hydrogel.

16. The apparatus of claim 1, wherein at least one of said threads comprises polyester.

17. The apparatus of claim 1, wherein said threads comprise non-planar surfaces at tips thereof.

18. The apparatus of claim 1, wherein said sensing zone is adjustable between being L-shaped and being Z-shaped.

* * * * *